US008403584B2

United States Patent
Stange et al.

(10) Patent No.: US 8,403,584 B2
(45) Date of Patent: Mar. 26, 2013

(54) DISPENSING OPENING PLATE FOR OPTICALLY ATTRACTIVE ANTIPERSPIRANT FORMULATIONS

(75) Inventors: Klaus-Peter Stange, Wentorf (DE); Stefan Ruester, Hamburg (DE); Stefan Biel, Hamburg (DE); Sabine Ripke, Hamburg (DE)

(73) Assignee: Beiersdorf AG, Hamburg (DE)

( * ) Notice: Subject to any disclaimer, the term of this patent is extended or adjusted under 35 U.S.C. 154(b) by 604 days.

(21) Appl. No.: 12/598,326

(22) PCT Filed: Mar. 19, 2008

(86) PCT No.: PCT/EP2008/002180
§ 371 (c)(1),
(2), (4) Date: Jan. 15, 2010

(87) PCT Pub. No.: WO2008/138421
PCT Pub. Date: Nov. 20, 2008

(65) Prior Publication Data
US 2010/0129135 A1    May 27, 2010

(30) Foreign Application Priority Data
May 9, 2007   (DE) .......................... 10 2007 022 255

(51) Int. Cl.
*B43K 1/06*    (2006.01)
(52) U.S. Cl. ......................................... 401/265; 401/261
(58) Field of Classification Search .................. 401/261, 401/263, 265, 266; 209/233
See application file for complete search history.

(56) References Cited

U.S. PATENT DOCUMENTS

| 611,485 | A | * | 9/1898 | Hosfeld ........................ 401/207 |
| 5,758,802 | A | * | 6/1998 | Wallays ........................ 222/212 |
| 5,813,785 | A | | 9/1998 | Baudin et al. |
| 5,833,382 | A | | 11/1998 | Jenks et al. |
| 6,745,781 | B2 | * | 6/2004 | Gueret ........................ 132/320 |
| 6,793,915 | B1 | | 9/2004 | Guenin et al. |
| 6,805,855 | B2 | | 10/2004 | Mattai et al. |
| 2002/0121530 | A1 | | 9/2002 | Socier |
| 2003/0235545 | A1 | | 12/2003 | Guenin et al. |
| 2004/0175346 | A1 | | 9/2004 | Guenin et al. |
| 2004/0180013 | A1 | | 9/2004 | Mattai et al. |
| 2004/0228886 | A1 | | 11/2004 | Ding et al. |
| 2004/0232169 | A1 | | 11/2004 | Glover et al. |

FOREIGN PATENT DOCUMENTS

| DE | 199 21 662 A1 | 11/2000 |
| EP | 0 312 165 A2 | 4/1989 |
| GB | 773761 | 5/1957 |
| WO | 91/04690 A1 | 4/1991 |
| WO | 00/08970 A1 | 2/2000 |

OTHER PUBLICATIONS

English language abstract of DE 199 21 662, Nov. 2, 2000.

* cited by examiner

*Primary Examiner* — David Walczak
(74) *Attorney, Agent, or Firm* — Abel Law Group, LLP

(57) ABSTRACT

A dispensing opening plate for applicators for cosmetic preparations. The plate comprises at least one dispensing opening that comprises one or more teeth or prongs which extend from an inner wall of the opening into a center of the opening.

20 Claims, 2 Drawing Sheets

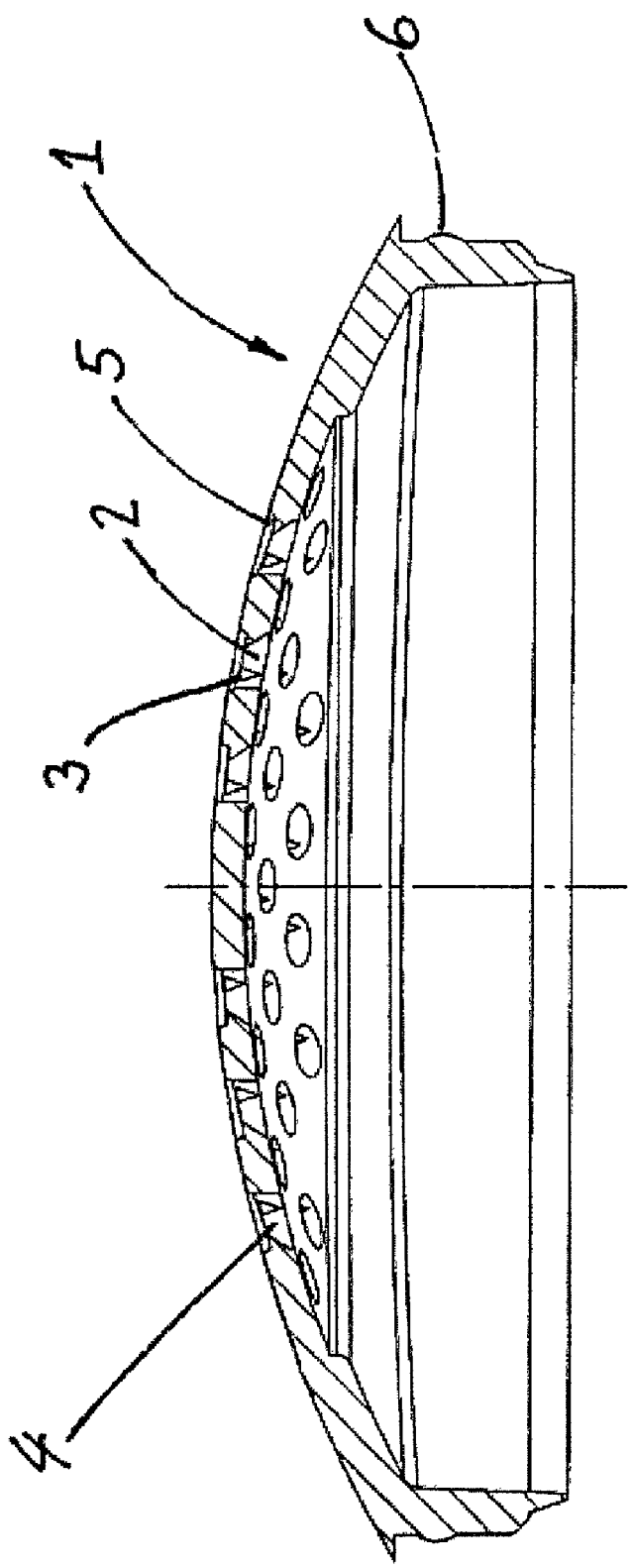

DISPENSING OPENING PLATE FOR OPTICALLY ATTRACTIVE ANTIPERSPIRANT FORMULATIONS

BACKGROUND OF THE INVENTION

1. Field of the Invention

The invention relates to a dispensing-opening plate for dispenser containers which are suitable for the application of cosmetic antiperspirant formulations containing stabilized particles.

2. Discussion of Background Information

Transparent and translucent products are preferred by many consumers, in particular, esthetically. Transparent formulations are thus frequently used, for example, as deodorants or antiperspirants. These preparations are often enriched with particles, so-called beads. Such preparations containing free-floating particles are known, for example, from DE 10200505551 A, U.S. Pat. No. 6,793,915 B and US 2004/022 88 86 A.

The production of cosmetic preparations which contain free-floating particles is therefore familiar to a person skilled in the art and does not pose any problem.

The particles incorporated in the cosmetic preparations may be very varied in type, e.g. of homogeneous or heterogeneous construction, in the form of active-substance-containing capsules or only to enhance the visual appeal of the preparation.

In all cases, however, the particles must have a certain level of hardness or strength in order that they are not destroyed or broken up during the production process of the preparation. However, this also means that it is only by subjecting them to a certain level of force during application that the particles can be ground down or broken up and distributed more or less homogeneously, mixed in with the rest of the preparation surrounding them.

This is generally not problematic in the case of shower products, since the latter are applied to the body generally by hand, a certain quantity of preparation being applied to the hand from the bottle and the hand then being guided, with a certain level of pressure, over the rest of the body in order to apply the preparation.

With deodorant products, the preparation is generally not applied directly by hand to the parts of the body which are deodorized; rather, this is done using applicators suitable for the applications. It has been found that the applicators known from the prior art—e.g. dispenser sticks with a spindle drive—function wonderfully well for preparations which do not contain any free-floating particles. Suitable dispensers are already known from Curtis Helene Ind's., U.S. Pat. No. 5,833,382, Procter & Gamble's EP 031 21 65, Unilever's EP 111 37 35, Gilette's DE 690 32 947 and Henkel KGaA's DE 199 21 662. Such dispensers generally have a dispensing-opening plate which may be connected in one or more pieces with the rest of the dispenser housing and carries one or more dispensing openings. The dispensing-opening plate is usually curved and/or rounded, this allowing it to slide easily over the area of skin envisaged for the application, in particular the armpit. It is important that even relatively pronounced application pressure does not result in any injuries in the application zone.

In the case of preparations which contain free-floating particles, however, the particles are ground down to an inadequate extent, in which case they remain on the skin in an undesirably intact state. It has been found that, here, the surface of the applicator, which in contrast to the palm of the hand is smooth, makes a significant contribution to the inadequate grinding down of the particles since the particles only "roll" between the applicator surface and the skin. Particles within the meaning of this application are understood to be in particular solids and liquids, for example solid beads or liquid droplets, which preferably have a size of 200 nm to a number of millimeters, preferably between 0.5 mm and 5 mm.

The situation is made more difficult, in addition, by the fact that particles which remain in the outlet opening when the product is ground down on the surface of the skin, and are therefore not exposed to any shearing action by the grinding-down operation, remain as intact particles, as a result of the product film applied to the skin, when the applicator is raised off from the skin.

A further phenomenon which renders application more difficult may also occur in the case of conventional dispensing openings: particles which have already been dispensed are pushed back ("collected") into the outlet openings again when the contents are distributed over the skin, in which case the quantity of effectively applied particles vastly decreases. This "vacuum cleaner effect" is successfully prevented by using the inventive dispensing-opening plates or dispensing openings.

It is an object of the present invention to provide a dispensing-opening plate which is suitable for dispenser containers which can be used to apply cosmetic preparations having at least one type of free-floating particles.

SUMMARY OF THE INVENTION

The present invention provides a dispensing opening plate for applicators for cosmetic preparations. The plate comprises at least one dispensing opening that comprises one or more teeth or prongs which extend from an inner wall of the opening into a center of the opening.

In one aspect, the smallest free diameter ($d_f$) of the at least one dispensing opening defined by the teeth or prongs may be smaller than the largest free diameter ($d_i$) without the teeth or prongs by 10% to 50%.

In another aspect, the smallest free diameter ($d_f$) of the at least one dispensing opening defined by the teeth or prongs may be from 0.5 mm to 3 mm and/or the largest free diameter ($d_i$) of the at least one dispensing opening without the teeth or prongs may be from 1 mm to 5 mm.

In yet another aspect, the at least one dispensing opening may be substantially frustoconical in shape, the larger diameter thereof being present on the surface side which is oriented toward the interior of a container which comprises a product which is to pass the opening.

In a still further aspect, the periphery of the dispensing opening may be rounded or may be provided with a chamfer or hollow.

The present invention also provides a container for a cosmetic preparation, which container comprises the dispensing opening plate of the present invention set forth above (including the various aspect thereof). The cosmetic preparation comprises particles. In one aspect of the container, the particles may have a diameter of from 0.5 mm to 5 mm.

In another aspect, the ratio of the average diameter of the particles to the diameter of the at least one dispensing opening may be from 1:1 to 0.8:1.

In yet another aspect, the teeth or prongs may be positioned in the dispensing opening such that they are offset inward into the dispensing opening, as seen from the outer dispensing opening plate surface, by a distance ($d_z$) which corresponds to 10% to 75% of the average particle diameter.

In a still further aspect, the cosmetic preparation may be an antiperspirant preparation and/or a deodorant preparation. For example, the preparation may be present in the form of a gel.

BRIEF DESCRIPTION OF THE DRAWINGS

In the appended drawings,

FIG. 2 shows a cross section of the dispensing opening plate shown in FIG. 1.

DETAILED DESCRIPTION OF THE INVENTION

Figure 1:
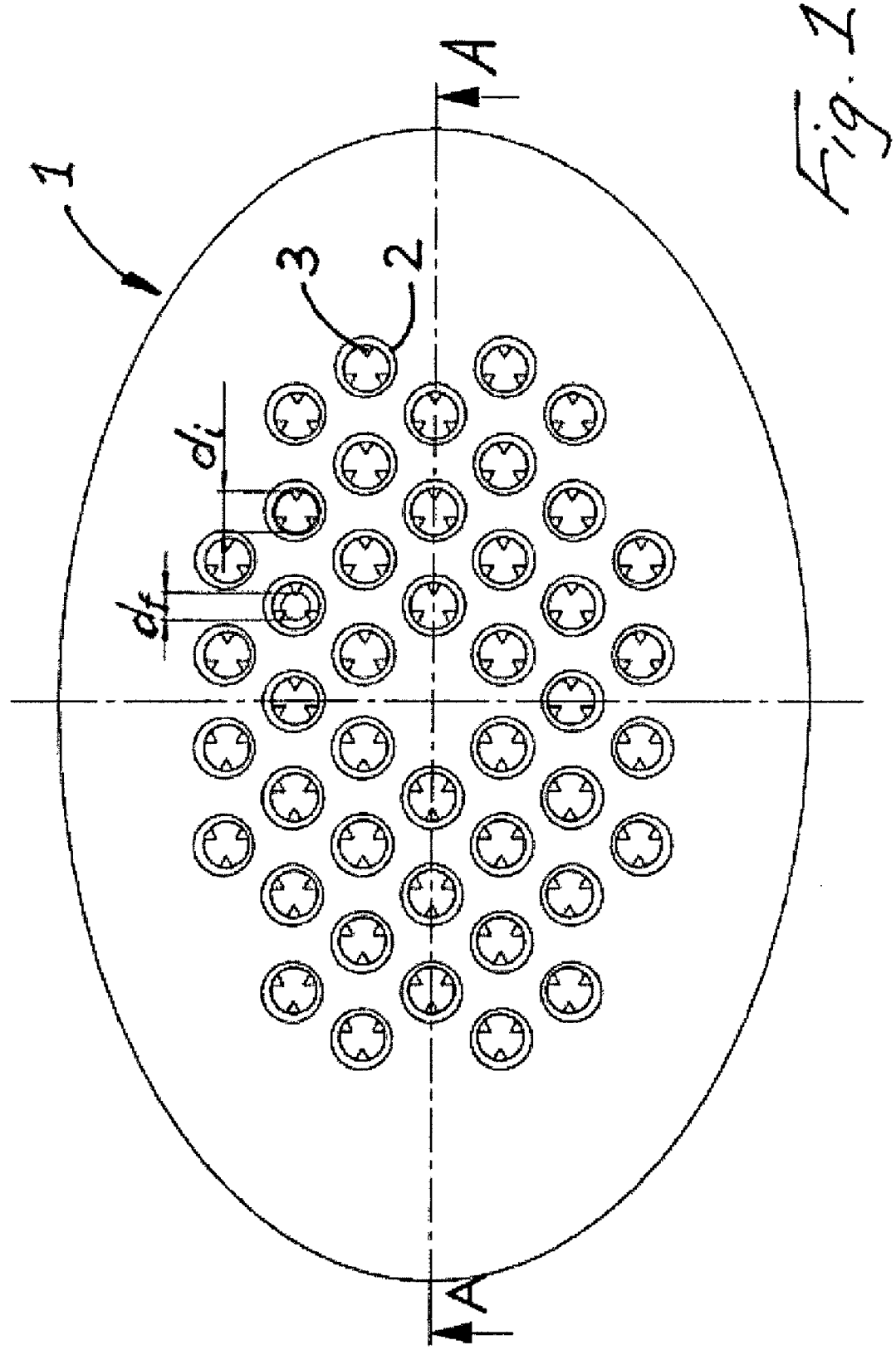
FIG. 1 shows a plan view of a dispensing opening plate according to the present invention.

It was surprising, and could not have been foreseen by a person skilled in the art, that dispensing-opening plates of which the dispensing opening(s) has (have), on the inside, at least one tooth or prong which projects into the free through-passage assist particles contained in cosmetic preparations in being ground down.

The important factor here is that the diameter of the dispensing openings is selected such that most of the particles can pass through these openings without blocking the opening. As they pass through the dispensing opening, the particles are nipped or split by the teeth or prongs projecting into the opening, as a result of which the spherical shape is lost. The no longer spherical particles can then easily be ground down during application.

Using the dispensing-opening plates according to the invention usually ensures that the particles are ground down in a residue-free manner.

It is advantageous according to the invention if the ratio of the average diameter of the particles to the diameter of the dispensing openings is in the range of 1:1 to 0.5:1. With a diameter ratio of greater than 1.1:1, the dispensing openings block very easily and preparation can be applied only unsatisfactorily, if at all.

It is advantageous if the prongs or teeth reduce the dispensing-opening diameter, i.e. the largest free diameter, such that the smallest free diameter, taking account of the teeth or prongs, is smaller by 10 to 50%.

A quite particularly advantageous dispensing-opening diameter has been found to be a diameter of 1.5 mm±0.5 mm, the dispensing-opening diameter always being measured in accordance with the largest free diameter, without taking account of the teeth or prongs, and the inwardly projecting teeth reducing the free opening to 1 mm±0.5 mm.

In a further particularly advantageous embodiment, the teeth are positioned below the outer grid surface, which has a decisive effect on the success of the particles being ground down on the skin. The positioning of the teeth or prongs in the dispensing openings appears to be advantageous in particular if these teeth or prongs are offset inward into the dispensing opening (as seen from the outer grid surface) by 10 to 75% of the average particle diameter.

It also falls within the context of the invention for the dispensing openings to have an ellipsoidal cross section rather than being round.

Another improved embodiment has dispensing openings which, rather than being cylindrical, are basically frustoconical in shape, in which case they deviate slightly from the cylindrical shape, the larger diameter being present on the surface side which is oriented toward the interior of the container.

Furthermore, it is advantageous for the outwardly oriented periphery of the dispensing opening to be rounded or to be provided with a chamfer or hollow. This considerably improves the sliding properties on the skin.

In order to ensure that the preparation is transferred completely onto the skin from the applicator surface, it is additionally advantageous if the applicator surface does not have any other structured formations, apart from the dispensing openings, e.g. scores or grooves, that are conductive to the grinding down of the particles.

The dispensing-opening plates according to the invention allow the particles contained in cosmetic preparations to be applied to particularly good effects with grinding-down actions.

The dispensing-opening plates can be fixed in the applicator by way of customary structures or auxiliary means, for example by way of latching, adhesive bonding or welding.

Quite particularly suitable formulations are those which have the particles in a free-floating state in the formulation, i.e., even if the product is not used for a relatively long period of time, the gravitational force does not cause the particles in the formulation to sink.

FIGS. 1 and 2 represent, by way of example, a dispensing-opening plate which has been found to be particularly advantageous. However, rather than having a limiting effect on the invention, this example is intended to illustrate the freedom of design available.

FIG. 1 shows the plan view of the dispensing-opening plate (1) which has a total of 44 dispensing openings (2). Each dispensing opening has three teeth (3) which extend from the inner wall of the dispensing opening into the center of the dispensing opening. The internal diameter $d_i$ (largest free diameter) of each dispensing opening (2) is 1.5 mm, and this results in a free cross section (smallest free diameter taking account of the teeth or prongs) of $d_f$=1 mm.

FIG. 2 shows a cross section (A-A) of the dispensing-opening plate (1) illustrated in FIG. 1. The teeth (3) are set back from the outer surface of the dispensing-opening plate. The dispensing openings (2) have, on the outside, a hollow (5) which extends almost as far as the top edge of the teeth (3). The dispensing openings (2) are frustoconical (4). In order to anchor it in the applicator, the dispensing-opening plate has a latching groove (6) all the way around it.

What is claimed is:

1. A container which comprises a cosmetic preparation therein, wherein the cosmetic preparation comprises particles and the container comprises a dispensing opening plate, which plate comprises at least one dispensing opening that comprises one or more teeth or prongs which extend from an inner wall of the opening into a center of the opening, a ratio of an average diameter of the particles to a diameter of the at least one dispensing opening being from 1:1 to 0.5:1.

2. The container of claim 1, wherein the particles have a diameter of from 0.5 mm to 5 mm.

3. The container of claim 1, wherein a ratio of an average diameter of the particles to a diameter of the at least one dispensing opening is from 1:1 to 0.8:1.

4. The container of claim 1, wherein a smallest free diameter ($d_f$) of the at least one dispensing opening defined by the teeth or prongs is smaller than a largest free diameter ($d_i$) without the teeth or prongs by 10% to 50%.

5. The container of claim 1, wherein a smallest free diameter ($d_f$) of the at least one dispensing opening defined by the teeth or prongs is from 0.5 mm to 3 mm.

6. The container of claim 1, wherein a largest free diameter ($d_i$) of the at least one dispensing opening without the teeth or prongs is from 1 mm to 5 mm.

7. The container of claim 1, wherein a diameter of the at least one dispensing opening is from 1 mm to 2 mm, the teeth or prongs reducing a free opening to from 0.5 mm to 1.5 mm.

8. The container of claim 1, wherein the at least one dispensing opening is substantially frustoconical in shape, a larger diameter thereof being present on a surface side which is oriented toward an interior of the container.

9. The container of claim 1, wherein a periphery of the dispensing opening is one of rounded and provided with a chamfer or hollow.

10. The container of claim 1, wherein the teeth or prongs are positioned in the dispensing opening such that they are offset inward into the dispensing opening, as seen from an outer dispensing opening plate surface, by a distance which corresponds to 10% to 75% of the average particle diameter.

11. The container of claim 1, wherein the particles are nipped or split by the teeth or prongs projecting into the at least one dispensing opening as they pass through the opening.

12. The container of claim 1, wherein the preparation is at least one of an antiperspirant preparation and a deodorant preparation.

13. The container of claim 12, wherein the preparation is in gel form.

14. The container of claim 1, wherein the particles are free-floating.

15. A container which comprises a cosmetic preparation therein, wherein the cosmetic preparation is at least one of an antiperspirant preparation and a deodorant preparation in gel form which comprises therein free-floating particles having a diameter of from 0.5 mm to 5 mm and wherein the container comprises a dispensing opening plate, which plate comprises at least one dispensing opening that comprises one or more teeth or prongs which extend from an inner wall of the opening into a center of the opening, a ratio of an average diameter of the particles to a diameter of the at least one dispensing opening being from 1:1 to 0.8:1.

16. The container of claim 15, wherein a smallest free diameter ($d_f$) of the at least one dispensing opening defined by the teeth or prongs is smaller than a largest free diameter ($d_i$) without the teeth or prongs by 10% to 50%.

17. The container of claim 15, wherein a smallest free diameter ($d_f$) of the at least one dispensing opening defined by the teeth or prongs is from 0.5 mm to 3 mm.

18. The container of claim 17, wherein a largest free diameter ($d_i$) of the at least one dispensing opening without the teeth or prongs is from 1 mm to 5 mm.

19. The container of claim 15, wherein the teeth or prongs are positioned in the dispensing opening such that they are offset inward into the dispensing opening, as seen from an outer dispensing opening plate surface, by a distance which corresponds to 10% to 75% of the average particle diameter.

20. The container of claim 15, wherein the particles are nipped or split by the teeth or prongs projecting into the at least one dispensing opening as they pass through the opening.

* * * * *